US007037505B2

(12) United States Patent
Kim et al.

(10) Patent No.: US 7,037,505 B2
(45) Date of Patent: May 2, 2006

(54) METHOD OF INDUCING PRODUCTION OF IL-8 OR TNF BY IN VITRO ADMINISTRATION OF AN N-TERMINAL POLYPEPTIDE OF P43

(75) Inventors: Sunghoon Kim, Seoul (KR); Young-Gyu Ko, Gyeonggi-do (KR)

(73) Assignee: Imagene Co., Ltd., Gyeonggi-Do (KR)

( * ) Notice: Subject to any disclaimer, the term of this patent is extended or adjusted under 35 U.S.C. 154(b) by 82 days.

(21) Appl. No.: 10/823,730

(22) Filed: Apr. 14, 2004

(65) Prior Publication Data
US 2004/0185060 A1    Sep. 23, 2004

Related U.S. Application Data

(63) Continuation of application No. 09/930,169, filed on Aug. 16, 2001, now abandoned.

(30) Foreign Application Priority Data
Jun. 5, 2001    (KR) ............................. 2001-31310

(51) Int. Cl.
A61K 38/16    (2006.01)
(52) U.S. Cl. .................................. 424/198.1; 530/350
(58) Field of Classification Search ............. 424/185.1, 424/198.1; 530/350; 514/2
See application file for complete search history.

(56) References Cited

FOREIGN PATENT DOCUMENTS

WO    WO 00/73801 A2    12/2000

OTHER PUBLICATIONS

Abbas et al., (1994) Cellular and Molecular Immunology 2nd ed., p. 75.*
Norcum et al. (2000) The Cytokine Portion of p43 Occupies a Central Position within the Eukaryotic Multisynthetase Complex J. Bio. Chem. 275:17921-17924.*
Ross et al. (2001) A compaison of gene espressin signatures from breast tumors and breast tissue derived lines. Disease Markers. 17:99-109.*
Quevillon, S. et al. "The p43 Component of the Mammalian Multi-synthetase Complex Is Likely to be the Precursor of the Endothelial Monocyte-activating Polypetide II Cytokine", J.Biol.Chem. (1997), vol. 272, No. 51, pp. 32573-32579, The American Society for Biochemistry and Molecular Biology, Inc.
Behrensdorf, H. et al. "The endothelial monocyte-activating polypeptide II (EMAP II) is a substrate for caspase-7" FEBS Lett., (2000), vol. 466, pp. 143-147, Federation of European Biochemical Societies.
Kao, J. et al. "A Peptide Derived from the Amino Terminus of Endothelial-Monocyte-activating Polypeptide II Modulates Mononuclear and Polymorphonuclear Leukocyte Functions, Defines an Apparently Novel Cellular Interaction Site, and Induces an Acute Inflammatory Response", J. Biol. Chem. (1994), vol. 269, No. 13, pp. 9774-9782, The American Society for Biochemistry and Molecular Biology, Inc.
Kao, J. et al. "Endothelial Monocyte-activating Polypeptide II: A Novel Tumor-Derived Polypeptide That Activates Host-Response Mechanisms", J. Biol. Chem. (1992), vol. 267, No. 28, pp. 20239-20247, The American Society for Biochemistry and Molecular Biology, Inc.
Kao, J. et al. "Characterization of a Novel Tumor-derived Cytokine: Endothelial-Monocyte Activating", J. Biol. Chem. (1994), vol. 269, No. 40, pp. 25106-25119, The American Society for Biochemistry and Molecular Biology, Inc.
Knies, U.E. et al., "Regulation of endothelial monocyte-activating polypeptide II release by apoptosis", Proc. Natl. Acad. Sci. USA (1998), vol. 95, pp. 12322-12337.
Schwarz, M.A. et al., "Endothelial-Monocyte Activating Polypeptide II, A Novel Antitumor Cytokine that Suppresses Primary and Metastatic Tumor Growth and Induces Apoptosis in Growing Endothelial Cells", J. Exp. Med. (1999) vol. 190, No. 3, pp. 341-352, The Rockefeller University Press.
Tas, M.P.R. and Murray, J.C., "Endothelial-Monocyte-Activating Polypeptide II", Int. J. Biochem. Cell. Biol. (1996), vol. 28, No. 8, pp. 837-841, 1996 Elsevier Science Ltd.
Schluesener, H.J. et al., "Localization of Endothelial-Monocyte-Activating Polypeptide II (EMAP II), a Novel Proinflammatory Cytokine, to Lesions of Experimental Autoimmune Encephalomyelitis, Neuritis, and Uveitis", GLIA (1997), vol. 20, pp. 365-372, Wiley-Liss, Inc.
Berger, A.C. et al., "Endothelial Monocyte-Activating Polypeptide II, a Tumor-Derived Cytokine That Plays an Important Role in Inflammation, Apoptosis, and Angiogenesis", J. Immunother. (2000), vol. 23, No. 5, pp. 519-527, Lippincott, Williams and Wilkins, Inc.
Ko, Y.G. et al., "A Cofactor of tRNA Synthetase, p43, Is Secreted to Up-regulate Proinflammatory Genes", J. Biol. Chem. (2001), vol. 276, No. 25, pp. 23026-23033, The American Society for Biochemistry and Molecular Biology, Inc.
Park, S.G. et al., "Precursor of Pro-apoptotic Cytokine Modulates Aminoacylation Activity of tRNA Synthetase", J. Biol. Chem. (1999), vol. 274, No. 24, pp. 16673-16676, The American Society for Biochemistry and Molecular Biology, Inc.

* cited by examiner

*Primary Examiner*—Deborah Crouch
*Assistant Examiner*—Louis D. Lieto
(74) *Attorney, Agent, or Firm*—Foley & Lardner LLP

(57) ABSTRACT

The present invention relates to an immunological enhancement agent, more particularly, to an immunological enhancement agent comprising peptide having an amino acid sequence represented by SEQ ID NO:1 to SEQ ID NO:3 as an effective component.

The peptides according to the present invention comprising the N-terminal domain of the p43 protein have excellent cytokine activity to improve an immune response so that they can be used as an effective immunological enhancement agent.

1 Claim, 1 Drawing Sheet

[FIG.1]
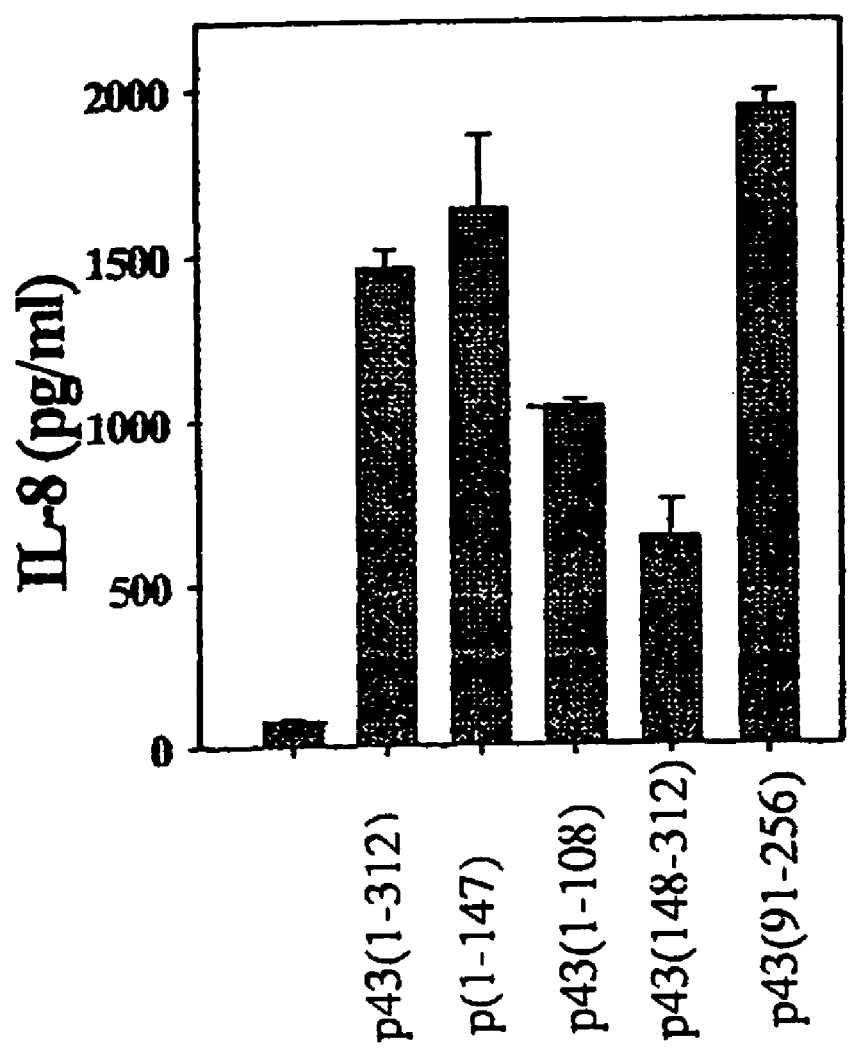

SEQUENCE LISTING

```
<160> NUMBER OF SEQ ID NOS: 11

<210> SEQ ID NO 1
<211> LENGTH: 147
<212> TYPE: PRT
<213> ORGANISM: mammalian

<400> SEQUENCE: 1

Met Ala Asn Asn Asp Ala Val Leu Lys Arg Leu Glu Gln Lys Gly Ala
 1               5                  10                  15

Glu Ala Asp Gln Ile Ile Glu Tyr Leu Lys Gln Gln Val Ser Leu Leu
            20                  25                  30

Lys Glu Lys Ala Ile Leu Gln Ala Thr Leu Arg Glu Glu Lys Lys Leu
        35                  40                  45

Arg Val Glu Asn Ala Lys Leu Lys Lys Glu Ile Glu Glu Leu Lys Gln
    50                  55                  60

Glu Leu Ile Gln Ala Glu Ile Gln Asn Gly Val Lys Gln Ile Ala Phe
65                  70                  75                  80

Pro Ser Gly Thr Pro Leu His Ala Asn Ser Met Val Ser Glu Asn Val
                85                  90                  95

Ile Gln Ser Thr Ala Val Thr Thr Val Ser Ser Gly Thr Lys Glu Gln
            100                 105                 110

Ile Lys Gly Gly Thr Gly Asp Glu Lys Lys Ala Lys Glu Lys Ile Glu
        115                 120                 125

Lys Lys Gly Glu Lys Lys Glu Lys Lys Gln Gln Ser Ile Ala Gly Ser
    130                 135                 140

Ala Asp Ser
145

<210> SEQ ID NO 2
<211> LENGTH: 108
<212> TYPE: PRT
<213> ORGANISM: mammalian

<400> SEQUENCE: 2

Met Ala Asn Asn Asp Ala Val Leu Lys Arg Leu Glu Gln Lys Gly Ala
 1               5                  10                  15

Glu Ala Asp Gln Ile Ile Glu Tyr Leu Lys Gln Gln Val Ser Leu Leu
            20                  25                  30

Lys Glu Lys Ala Ile Leu Gln Ala Thr Leu Arg Glu Glu Lys Lys Leu
        35                  40                  45

Arg Val Glu Asn Ala Lys Leu Lys Lys Glu Ile Glu Glu Leu Lys Gln
    50                  55                  60

Glu Leu Ile Gln Ala Glu Ile Gln Asn Gly Val Lys Gln Ile Ala Phe
65                  70                  75                  80

Pro Ser Gly Thr Pro Leu His Ala Asn Ser Met Val Ser Glu Asn Val
                85                  90                  95

Ile Gln Ser Thr Ala Val Thr Thr Val Ser Ser Gly
```

```
<210> SEQ ID NO 3
<211> LENGTH: 166
<212> TYPE: PRT
<213> ORGANISM: mammalian

<400> SEQUENCE: 3

Met Val Ser Glu Asn Val Ile Gln Ser Thr Ala Val Thr Thr Val Ser
  1               5                  10                  15

Ser Gly Thr Lys Glu Gln Ile Lys Gly Thr Gly Asp Glu Lys Lys
             20                  25                  30

Ala Lys Glu Lys Ile Glu Lys Lys Gly Glu Lys Lys Glu Lys Lys Gln
         35                  40                  45

Gln Ser Ile Ala Gly Ser Ala Asp Ser Lys Pro Ile Asp Val Ser Arg
     50                  55                  60

Leu Asp Leu Arg Ile Gly Cys Ile Ile Thr Ala Arg Lys His Pro Asp
 65                  70                  75                  80

Ala Asp Ser Leu Tyr Val Glu Glu Val Asp Val Gly Glu Ile Ala Pro
                 85                  90                  95

Arg Thr Val Val Ser Gly Leu Val Asn His Val Pro Leu Glu Gln Met
                100                 105                 110

Gln Asn Arg Met Val Ile Leu Leu Cys Asn Leu Lys Pro Ala Lys Met
            115                 120                 125

Arg Gly Val Leu Ser Gln Ala Met Val Met Cys Ala Ser Ser Pro Glu
        130                 135                 140

Lys Ile Glu Ile Leu Ala Pro Pro Asn Gly Ser Val Pro Gly Asp Arg
145                 150                 155                 160

Ile Thr Phe Asp Ala Phe
                165

<210> SEQ ID NO 4
<211> LENGTH: 27
<212> TYPE: DNA
<213> ORGANISM: Artificial Sequence
<220> FEATURE:
<223> OTHER INFORMATION: PCR primer

<400> SEQUENCE: 4
ccggaattca tggcaaataa tgatgct                                              27

<210> SEQ ID NO 5
<211> LENGTH: 24
<212> TYPE: DNA
<213> ORGANISM: Artificial Sequence
<220> FEATURE:
<223> OTHER INFORMATION: PCR primer

<400> SEQUENCE: 5
ctggtcgacg tcggcacttc cagc                                                 24

<210> SEQ ID NO 6
<211> LENGTH: 32
<212> TYPE: DNA
<213> ORGANISM: Artificial Sequence
<220> FEATURE:
<223> OTHER INFORMATION: PCR primer

<400> SEQUENCE: 6
cggaattcat ggtttctgaa aatgtgatac ag                                        32
```

```
<210> SEQ ID NO 7
<211> LENGTH: 30
<212> TYPE: DNA
<213> ORGANISM: Artificial Sequence
<220> FEATURE:
<223> OTHER INFORMATION: PCR primer

<400> SEQUENCE: 7
ccggtcgact cagaaagcat caaagtaatt                              30

<210> SEQ ID NO 8
<211> LENGTH: 18
<212> TYPE: DNA
<213> ORGANISM: Artificial Sequence
<220> FEATURE:
<223> OTHER INFORMATION: PCR primer

<400> SEQUENCE: 8
catatggcaa ataatgat                                           18

<210> SEQ ID NO 9
<211> LENGTH: 18
<212> TYPE: DNA
<213> ORGANISM: Artificial Sequence
<220> FEATURE:
<223> OTHER INFORMATION: PCR primer

<400> SEQUENCE: 9
ctcgagggaa gcatttta                                           18

<210> SEQ ID NO 10
<211> LENGTH: 27
<212> TYPE: DNA
<213> ORGANISM: Artificial Sequence
<220> FEATURE:
<223> OTHER INFORMATION: PCR primer

<400> SEQUENCE: 10
ccggaattct ctaagccaat agatgtt                                 27

<210> SEQ ID NO 11
<211> LENGTH: 27
<212> TYPE: DNA
<213> ORGANISM: Artificial Sequence
<220> FEATURE:
<223> OTHER INFORMATION: PCR primer

<400> SEQUENCE: 11
ccggtcgact tatttgattc cactgtt                                 27
```

METHOD OF INDUCING PRODUCTION OF IL-8 OR TNF BY IN VITRO ADMINISTRATION OF AN N-TERMINAL POLYPEPTIDE OF P43

This application is a Continuation application of Ser. No. 09/930,169, filed Aug. 16, 2001 now abandoned, which claims priority from Korean patent application 2001-31310, filed Jun. 5, 2001.

FIELD OF THE INVENTION

The present invention relates to an immunological enhancement agent, more particularly, to an immunological enhancement agent comprising specific peptides having immunological activity as an effective component.

BACKGROUND OF THE INVENTION

Cells undergoing programmed cell-death (known as apoptosis) are rapidly removed by monocyte-derived macrophages. This phenomenon infers that apoptotic cells might secrete specific factors and these factors cause chmotaxis to leucocyte and monocyte. The endothelial monocyte-activating polypeptide II (hereinafter, referred to as "EMAP II") is known as one of the specific factors because it is released from the apoptotic cells and causes chemotaxis.

The EMAP II is the C-terminal domain of the p43 protein—the precursor of the EMAP II, consisting of 312 amino acids—and it is cleaved to form by caspase-7, in which aspartic acid—the 146th amino acid of p43 protein—is activated in apoptotic cells (Quevillion, S. et al., *J. Biol. Chem.*, 272:32573–32579, 1997; Behrensdorf, M. A. et al., *FEBS Lett.*, 466:143–147, 2000). The structure and maturation of the EMAP II is similar to that of an IL-1β, a cytokine involved in a proinflammatory response, and 14.5 kDa of the IL-1β is cleaved to form from 33 kDa of inactive pre-IL-1β by ICE (caspase-1). An EMAP II is the mediator of proinflammatory response that induces the expression of tissue factor, tumor necrosis factor (hereinafter, referred to as "TNF") and interleukin-8 (hereinafter, referred to as "IL-8") in mononuclear phagocyte and polymorphonuclear leucocytes. Also, in a tissue expressing a high level of EMAPII mRNA, macrophages are accumulated. This means that an EMAP II is a chemotaxis material leading macrophage to dead cells. It is known that the EMAP II acts as a cytokine, and the 15 amino acids of the N-terminal domain of an EMAP II play a vital role in the reaction (Quevillon, S. et al., *J. Biol. Chem.*, 272:32573–32579, 1997; Kao, J. et al., *J. Biol. Chem.*, 269:9774–7982, 1994; Kao, J. et al., *J. Biol. Chem.*, 267:20239–20247, 1992; Kao, J. et al., *J. Biol. Chem.*, 269:25106–25119, 1994; Knies, U. E. et al., PNAS USA, 95:12322–12327, 1998). In the U.S. Pat. No. 5,641,867, it is described that the N-terminal domain of an EMAP II that comprises arginine-isoleucine-glycine-arginine-isoleucine-threonine is an important residue in cytokine function of the EMAP II. Recently, it was reported that the EMAP II repressed the growth of primary and metastatic tumor in proliferating endothelial cells that are not causing particular side-effect in normal cell (Schwarz, M. A. et al., *J. Exp. Med.*, 190:341–353, 1999).

On the other hand, the p43 protein is expressed extensively. The expression level of p43 protein varies temporally and spatially, especially in a developing mouse. For example, it was shown that the expression of a p43 in the lung of mouse from 8 days to 16 days after its birth was increased dramatically. In addition, the p43 is highly expressed in the microglial cells in the lesions of autoimmune disease such as encephalomyelitis, neuritis and uveitis. The high expression level of the p43 in specific developmental stage and tissues suggests that the p43 could have unexpected functions in angiogenesis, inflammation, and apoptosis (Tas, M. P. R., and Marray, J. C., *Int. J. Biochem. Cell. Biol.*, 28:837–841, 1996; Schwarz, M. J. et al., *Glia*, 20:365–372, 1997; Schuesner, H. J. et al., *Glia*, 20:365–372, 1997; Berger, A. C. et al., *J. Immunother.*, 23:519–527, 2000).

As mentioned previously, the EMAP II—C-terminal domain of p43—has been studied extensively for its cytokine activities; however, p43 (i.e. pro-EMAP II) and its N-terminal domain have not been understood. Therefore, the present inventors have studied to disclose that a p43 can act as a more effective cytokine and as an immunological enhancement agent than the EMAP II. We did this by comparing cytokine activity of a p43 with that of an EMAP II, C-terminal domain of p43 in the PCT application No. PCT/KR00/00630.

The present inventors compared the secretion pattern of a p43 with that of an EMAP II in normal cells and apoptotic cells, and reported that the cytokine acting in physiological condition was the p43 and not the EMAP II. Since the EMAP II is secreted during the late stage of apoptosis in which cells are completely destroyed in normal cells, it is not active in the early stage of apoptosis; whereas, the p43 is constitutively secreted from various cells irrespectively of apoptosis (Ko Y G et al., A cofactor of tRNA synthetase, p43, is secreted to up-regulate proinflammatory genes, *J. Biol. Chem.* 2001, Apl 5, 276).

While studying the p43, the present inventors achieved the present invention by discovering that the peptides, including N-terminal domain of p43, showed an excellent cytokine activity with the result of estimating cytokine activities of deletion-mutants of the p43 protein.

SUMMARY OF THE INVENTION

It is an object of the present invention to provide an immunological enhancement agent that comprises the N-terminal domain of the p43 showing an excellent immunological activity as an effective component.

In order to accomplish the object above, the present invention provides an immunological enhancement agent that comprises a peptide having an amino acid sequence represented by SEQ ID NO:1 to SEQ ID NO:3 as an effective component.

According to the present invention, the p43(1–147), the p43(1–108) and the p43(91–256), which comprise the N-terminal domain of the p43 protein, can act as a cytokine to increase the amount of the TNF and the IL-8. As a result, they can improve an immune response and be used as an effective immunological enhancement agent.

BRIEF DESCRIPTION OF DRAWINGS

FIG. 1 illustrates the amount of IL-8 produced after incubation of human monocyte THP-1 cells to which the purified p43 protein and its deletion-mutants are added respectively.

DETAILED DESCRIPTION OF THE INVENTION

The present invention will be described in detail.

According to the present invention, the peptides that have an amino acid sequence—represented by SEQ ID NO:1 to SEQ ID NO:3 as an effective component of an immunological enhancement agent—are the N-terminal domain of the p43 protein. More particularly, these peptides consist of peptide having amino acids from 1 to 147 of the p43 protein, peptide from 1 to 108 of the p43 protein, and peptide from 91 to 256 of the p43 protein.

In order to obtain the peptides that comprise the N-terminal domain of the p43, first, the deletion-mutants of the p43 protein were constructed. Then they were purified and added to cultivated mammalian cells. Next, the degree of inducing the production of cytokine was measured. Finally, the peptides showing a high level of cytokine induction in cultivated mammalian cells could be isolated from various deletion-mutants of the p43 protein.

To indicate the p43 protein or its deletion-mutants, for the sake of convenience, the first and the last number of amino acid sequence of the p43 protein was used in parentheses; for example, the peptide having amino acids from 91 to 256 of the p43 was represented by "p43(91–256)".

In one embodiment of the present invention, recombinant vectors were respectively prepared according to known technique (Park, S. G. et al., *J. Biol. Chem.*, 274:166673–16676, 1999). The recombinant vectors include the following genes respectively encoding: the p43(1–312), which is the p43; the p43(148–312), which is the C-terminal domain of the p43 or the EMAPII; the p43(1–147), the p43(1–108), and the p43(91–256) which include N-terminal part of the p43. The vectors for cloning the above genes are not limited to specific vectors, but pET28a is preferable. The p43 protein and its deletion mutants can be expressed by transforming host cell with the prepared vectors including gene of the p43 or its deletion mutants. The host cell for transformation is not limited specifically, but *E. coli* is preferable.

In another embodiment of the present invention, the cytokine activity of the p43 and its deletion-mutants protein was investigated. The expressed proteins were added to a mammalian cell cultured in serum-free media, and the amount of inducing production of other cytokines was measured. The mammalian cell is not specifically limited if only it is a growth factor dependent cell, however, a human monocyte THP-1 cell is more preferable. Whether or not the above proteins have immunological activity was investigated by measuring the amount of cytokine produced that can be induced by the p43 or its deletion-mutant proteins. More particularly, among cytokines the amount of the TNF and the IL-8 produced was measured in the present invention. In order to measure the amount of produced cytokines, a well-known method in the art can be used, particularly, in the present invention, ELISA (Enzyme-Linked Immuno Sandwich Assay) was used.

The p43(1–147), the p43(1–108) and the p43(91–256), the peptides represented by SEQ ID NO:1 to SEQ ID NO:3 according to the present invention, showed cytokine activity and induced the production of the TNF and the IL-8. According to the results confirmed in the present invention, the produced amount of the TNF and the IL-8 induced by the above peptides was higher by 2–3 times more than that by EMAP II. The produced amount of the TNF and the IL-8 induced by the peptide represented by SEQ ID NO:1 was higher by 1.1 times more than by the p43 and higher by 2.5–3 times more than by EMAP II.

The immonological enhancement agent according to the present invention that comprises the N-terminal part of the p43 as an effective component is not limited to a specific form, if only it is a feasible form for being administered to human and animals. Also, it can be a form supported with carrier.

As the carrier, at least one of a solid, a liquefied diluent, a filling agent, and other assistant can be used with the ratio of 0.1~99.5%. The immunological enhancement agent can be administered orally or non-orally. The non-oral administration can be tissue partial-, hypodermal-, intramuscular-, arterial-, intravenous-, and rectal administration. The preferable administration form can be prepared in conventional techniques.

Oral administration can be done by using a solid or liquid form; for example, bulk powders, powders, granules, tablets, capsules, syrups, suspensions, etc. If necessary, the unit administration form for oral administration can be microcapsulated. The extension of the activity period and the sustained release of a formulation can be obtained by coating the formulation or inserting its active components to polymer or wax.

The administration amount of the immunological enhancement agent can be determined preferably by taking into consideration for the age of patient, the body weight, a method of administration, any disease and its state, and so on.

The present invention will be described in more detail by the following examples. However, it should be understood that these examples are provided only for the illustration of the present invention but not intended to limit the scope of the invention in any manner.

EXAMPLE 1

Preparation of Recombinant Vector Including p43(1–147) Gene, Protein Expression, and its Purification The recombinant vector, including the p43(1–147) gene, was prepared by known method in the art (Park, S. G. et al., *J. Biol. Chem.*, 274:16673–16676, 1999). Plasmid pM388 provided from Dr. Kiyotaka Shiba in Japan Cancer Institute was restricted with NdeI and XhoI to obtain the p43 gene, and it was used as a template. The PCR was performed using the forward and reverse primer represented by SEQ ID NO:4 and SEQ ID NO:5 respectively, under the condition as follows; 1 min at 95° C., 1 min at 58° C., and 1 min at 72° C. The resulting PCR product was restricted with EcoRI and SalI and inserted into pET28a (Novagen, Madison, USA) to prepare the recombinant vector.

*E. coli* BL21(DE3) was transformed with the above recombinant vector including the p43(1–147) gene. The transformed BL21 was cultured in 100 ml of LB medium (Luria Broth; 1 g NaCl, 1 g Bacto-tryptone, 0.5 g yeast extracts) and the p43(1–147) gene was expressed as a His-tag fusion protein form. The expressed p43(1–147) protein was purified by using nickel affinity chromatography and mono Q or S ion-exchange chromatography according to known method in the art (Park, S. G. et al., *J. Biol. Chem.*, 274:16673–16676, 1999). To remove lipopolysaceharide, which induces inflammatory response, the purified protein was dialyzed with the pyrogen-free buffer solution (10 mM potassium phosphate (pH 6.0), 100 mM NaCl) overnight. After dialysis, the protein was loaded to a polymyxin resin (Bio-Rad) that was equilibrated with the same buffer, incubated for 20 minutes and eluted. The concentration of the remaining lipopolysaceharide was measured using the Limulus Amebocyte lysate QCL-1000 kit (Bio Whittacker). As a result, the concentration of the lipopolysaceharide was below 20 pg/ml—not able to induce inflammatory response. The purified protein was then subjected to SDS-PAGE. It was confirmed that p43(1–147) protein having the molecular weight of 21 kDa was isolated purely(data not shown).

EXAMPLE 2

Preparation of Recombinant Vector Including p43(1–108) Gene, Protein Expression, and its Purification The recombinant vector, including the p43(1–108) gene, was prepared according to the same method described in the Example 1. The recombinant vector pET28a (Novagen) containing the p43(1–312) gene was restricted with AspI and SalI. The restricted recombinant vector was treated with the klenow fragment to fill up the DNA ends and re-ligated. And then, the recombinant vector, including the p43(1–108) gene, was prepared by treating ligase and making the vector self-ligation. BL21 was transformed with the recombinant vector, including the p43(1–108) gene, according to the same method described in the Example 1. The expressed p43(1–108) protein was purified and analyzed by SDS-PAGE.

As a result, it was confirmed that p43(1–108) protein having the molecular weight of 20 kDa was isolated purely (data not shown).

EXAMPLE 3

Preparation of Recombinant Vector Including p43 (91–256) Gene, Protein Expression, and its Purification The recombinant vector, including the p43(91–256) gene, was prepared according to the same method described in the Example 1, except that the PCR was performed using the forward and reverse primer represented by SEQ ID NO:6 and SEQ ID NO:7 respectively, under the condition as follows; 30 sec at 95° C., 30 sec at 50° C., and 40 sec at 72° C. BL21 was transformed with the recombinant vector, including the p43(91–256) gene, according to the same method described in the Example 1. The expressed p43 (91–256) protein was purified and analyzed by SDS-PAGE.

As a result, it was confirmed that p43(9 1–256) protein having the molecular weight of 29 kDa was isolated purely (data not shown).

EXAMPLE 4

Measurement of Cytokine Activity

To measure a cytokine activity of the deletion-mutant proteins of the p43 that was purified in the Example 1–3, the following experiment was performed.

The human monocyte THP-1 cells (supplied from the ATCC and cultured selecting the sensitive cells to lipopolysaceharide) were inoculated to the RPMI1640 medium containing 10% fetal bovine serum (FBS) and 50 mu.g/ml streptomycin and penicillin, and cultured in 5% $CO_2$ at 37° C. The cultured cells were washed twice with serum-free RPMI1640, and then $2 \times 10^6$ cells/ml were inoculated into 24-well plate containing 0.5 ml of serum-free RPMI1640 medium. The cells were cultured for 2 hours under the same condition, and stimulated for 4 hours by adding 100 nM of the proteins purified in the Example 1–3 respectively. The supernatants were collected, and the concentration of the TNF and the IL-8 was measured using the ELISA kit (PharMingen) according to the manufacturer's instructions. The stimulation experiments were repeated twice. The produced amount of W-8 was shown in FIG. 1.

Comparative Example 1

Preparation of Recombinant Vector Including p43(1–312) Gene, Protein Expression, and Measurement of Cytokine Activity The recombinant vector, including the p43(1–312) gene, was prepared according to the same method described in the Example 1, except that the PCR was performed using the forward and reverse primer represented by SEQ ID NO:8 and SEQ ID NO:9 respectively, and the pM338 as a template, and NdeI and XhoI were used as restriction enzymes. BL21 was transformed with the recombinant vector, including the p43(1–312) gene, according to the same method described in the Example 1. The expressed p43(1–312) protein was purified and analyzed by SDS-PAGE.

As a result, it was confirmed that p43(1–312) protein having the molecular weight of 42 kDa was isolated purely (data not shown).

To measure a cytokine activity of the purified p43(1–312) protein, the each produced amount of the TNF and the IL-8 was measured according to the same method described in the Example 4. The produced amount of IL-8 was shown in FIG. 1.

Comparative Example 2

Preparation of Recombinant Vector Including p43 (148–312) Gene, Protein Expression, and Measurement of Cytokine Activity The recombinant vector, including the p43(148–312) gene, encoding EMAP II was prepared according to the same method described in the Example 1, except that the PCR was performed using the forward and reverse primer represented by SEQ ID NO:10 and SEQ ID NO:11 respectively, and pM338 as a template. BL21 was transformed with the recombinant vector, including the p43(148–312) gene, according to the same method described in the Example 1. The expressed p43(148–312) protein was purified and analyzed by SDS-PAGE.

As a result, it was confirmed that p43(148–312) protein having the molecular weight of 26 kDa was isolated purely (data not shown).

To measure a cytokine activity of the purified p43 (148–312) protein, the each produced amount of the TNF and the IL-8 was measured according to the same method described in the Example 4. The produced amount of IL-8 was shown in FIG. 1.

Observing that the produced amount of the TNF induced by the p43(1–312)(p43 protein), the p43(148–312) (EMAPII) and the deletion-mutants of the p43 protein, i.e., p43(1–147), p43(1–108), and p43(91–256), as shown in FIG. 3, in case of p43(1–132the produced amount of TNF was 1,500 pg/ml, p43(148–312) was 500 pg/ml, p43(1–147) was 1,650 pg/ml, p43(1–108) was 1,000 pg/ml, and p43 (91–256) was 2,200 pg/ml. From these results, it was confirmed that the amount of the TNF produced by the p43(1–312)(p43 protein), and proteins comprising the N-terminal part of the p43 protein, i.e., p43(1–147), p43(1–108), and p43(91–256) was much more than that by the p43 (148–312)(EMAP II).

Observing that the produced amount of the IL-8 induced by the above proteins, as shown in FIG 1, in case of p43(1–132), the produced amount of IL-8 was 1,495 pg/ml, p43(148–312) was 650 pg/ml, p43(1–147) was 1,650 pg/ml, p43(1–108) was 1,050 pg/ml, and p43(91–256) was 1,950 pg/ml. From these results, it was confirmed that the amount of the IL-8 produced by p43(1–312) (p43 protein) and proteins comprising the N-terminal part of the p43 protein, i.e., p43(1–147), p43(1–108), and p43(91–256) was more than that by p43(148–312) (EMAP II).

In conclusion, it was confirmed that the p43(1–147), the p43(1–108), and the p43(91–256)—which comprise the N-terminal part of the p43 protein—showed by far higher cytokine activity than the EMAP II. The result illustrates that the N-terminal part of the p43 plays a vital role in the cytokine activity. Therefore, the peptides of the present invention comprising the N-terminal domain of the p43 can be used as an immunological enhancement agent showing an excellent cytokine activity.

What is claimed is:

1. A method of inducing production of LL-8 and TNF in vitro, comprising administering a polypeptide consisting of SEQ ID NO: 1 or SEQ ID NO: 2 to cells capable of producing IL-8 and TNF.

* * * * *